(12) United States Patent
Kondo

(10) Patent No.: US 7,416,587 B2
(45) Date of Patent: Aug. 26, 2008

(54) HEAT REGENERATIVE DEODORIZING FILTER

(75) Inventor: Yasuyoshi Kondo, Chiyoda-ku (JP)

(73) Assignee: Mitsubishi Paper Mills Limited, Tokyo (JP)

( * ) Notice: Subject to any disclaimer, the term of this patent is extended or adjusted under 35 U.S.C. 154(b) by 226 days.

(21) Appl. No.: 10/549,061

(22) PCT Filed: Mar. 9, 2004

(86) PCT No.: PCT/JP2004/003014

§ 371 (c)(1),
(2), (4) Date: Sep. 12, 2005

(87) PCT Pub. No.: WO2004/080497

PCT Pub. Date: Sep. 23, 2004

(65) Prior Publication Data

US 2006/0162566 A1    Jul. 27, 2006

(30) Foreign Application Priority Data

| Mar. 10, 2003 | (JP) | ............................... 2003-062630 |
| Mar. 13, 2003 | (JP) | ............................... 2003-068675 |
| Mar. 13, 2003 | (JP) | ............................... 2003-068676 |
| Mar. 27, 2003 | (JP) | ............................... 2003-087081 |

(51) Int. Cl.
*B01D 53/02* (2006.01)
*F25D 17/04* (2006.01)
*B60H 1/32* (2006.01)

(52) U.S. Cl. .............................. 96/146; 62/317; 62/239

(58) Field of Classification Search ................... 62/317, 62/239; 96/146
See application file for complete search history.

(56) References Cited

U.S. PATENT DOCUMENTS

| 4,652,727 | A | * | 3/1987 | Hoshizaki et al. ........... 219/541 |
| 5,954,577 | A | * | 9/1999 | Meckler ....................... 454/75 |
| 6,199,397 | B1 | * | 3/2001 | Khelifa et al. ................. 62/317 |

FOREIGN PATENT DOCUMENTS

| DE | 100 60 301 A1 | 1/2003 |
| JP | 59-115729 | 7/1984 |
| JP | 1-304704 | 6/1988 |
| JP | 1-304704 | 12/1989 |
| JP | 02-018006 | 1/1990 |
| JP | 3-67644 | 3/1991 |

(Continued)

OTHER PUBLICATIONS

International Search Report (dated Jun. 8, 2004).

(Continued)

*Primary Examiner*—Walter D. Griffin
*Assistant Examiner*—Amber Miller Harris
(74) *Attorney, Agent, or Firm*—John J. Penny, Jr.; Edwards Angell Palmer & Dodge LLP

(57) ABSTRACT

A thermally regenerative deodorizing filter, which comprises a deodorizing filter comprising a deodorant which is adaptable to a thermal regeneration and a honeycomb base material having a heat conductivity which carries the deodorant, and a heating element for regenerating the deodorizing filter which is integrated in the deodorizing filter, wherein the heating element is controlled to a predetermined temperature during the regeneration.

9 Claims, 9 Drawing Sheets

FOREIGN PATENT DOCUMENTS

| | | |
|---|---|---|
| JP | 5-047503 | 2/1993 |
| JP | 05-338065 | 12/1993 |
| JP | 07-016287 | 1/1995 |
| JP | 7-16287 | 1/1995 |
| JP | 7-16579 | 3/1995 |
| JP | 07-136628 | 5/1995 |
| JP | 8-66460 | 3/1996 |
| JP | 9-94292 | 4/1997 |
| JP | 1997-094292 * | 4/1997 |
| JP | 09-187662 | 7/1997 |
| JP | 10-15332 | 1/1998 |
| JP | 11-319489 | 11/1999 |
| JP | 2001-070418 | 3/2001 |
| JP | 2002-066223 | 3/2002 |

OTHER PUBLICATIONS

Supplemental European Search Report (dated Mar. 31, 2006).
Japanese Industrial Standard, "Corrugated Fibreboards for Shipping Containers," JIS Z 1516 (1985), translated and published by Japanese Standards Association.

* cited by examiner

HEAT REGENERATIVE DEODORIZING FILTER

TECHNICAL FIELD

The present invention relates to a thermally regenerative deodorizing filter which can be repeatedly used by heating. More specifically, the present invention relates to a thermally regenerative deodorizing filter integrated with a heating element, which is able to exhibit an aimed catalytic activity efficiently by using a temperature controllable PTC heater as the heating element to be used.

BACKGROUND ART

Hitherto, offensive smells industrially emitted in factories and the like and offensive smells derived from wastes in service industries such as restaurants and hotels have been considered to be problematic. Recently, bad smells in spaces of daily life such as in automobiles and in common rooms have come under closer scrutiny.

Therefore, there are increasing needs for removal of harmful substances such as these smells, and hence air cleaners integrated with a deodorizing apparatus or a deodorizing filter have been actively developed.

On the other hand, in consideration of the global environment, reduction in weight of wastes is desired and it becomes a problem that the deodorizing filter turns into waste after use. Thus, it is required to use the deodorant filter repeatedly by regeneration.

Some of recent home electric appliances such as air conditioners have adopted a mode of regenerating their deodorizing ability by cleaning a filter with water or a detergent after using (for example, see JP-2002-066223 and JP-2001-070418). However, it is necessary for a user to remove and wash the filter regularly, and therefore, a more convenient regeneration method is desired.

In recent air cleaners, filters containing active carbon are employed and a method of removing harmful substances such as offensive smells by adsorbing thereof on the active carbon is adopted.

Among all, a deodorizing filter in which particulate active carbon is packed into cells of a honeycomb and both openings of the honeycomb are sealed with a gas-permeable base material has a large amount of active carbon per a unit volume and exhibits a high gas-permeability taking the amount of active carbon into consideration. Thus, it is especially excellent as a deodorizing filter using active carbon and hence is employed in various air cleaners.

Among recent air cleaning equipments, an equipment mounted with a deodorizing filter which is packed with active carbon capable of regeneration by washing with water has been commercially available, but the washing operation is difficult. Further, in general, the washing with water can regenerate the filter when hot water is used, but complete regeneration effect cannot be obtained when low-temperature water like tap water is used. In addition, since the particulate active carbon is not easily dried after washing, more convenient and effective regeneration method is desired.

Recently, there has been a raw garbage disposer in which a plate-form heater is provided in close contact with a honeycomb surface of a catalyst to impart a mechanism of thermal regeneration at 200° C. to 300° C. when the catalyst reaches saturation for adsorption of odors and oxidative decomposition and its deodorizing ability decreases.

However, in general air conditioning equipments, continuous use is problematic since it is a rare case where a heat source capable of achieving such a high temperature of 200° C. or higher is available and, in the case of using a catalyst, regeneration efficiency by thermal treatment is remarkably lowered when the catalyst surface is covered with dirt, dust, and the like and hence the catalyst becomes physically impossible to work (cf. JP-A-7-136628).

As the other equipment, there is reported a deodorizing equipment in which regeneration of deodorization performance is intended by heating an absorbent through electrification of the adsorbent as a heating means of odor components. However, the deodorant should be an electroconductive substance or a material having no conductivity should be subjected to a treatment for suitable impartment of conductivity. In addition, even when the adsorbent is electrified, it is virtually difficult to achieve uniform electrification of all over the adsorbent of the whole filter to reach a constant elevated temperature, so that the equipment is not suitable for practical use (cf. JP-B-7-16579).

Furthermore, as a deodorizing filter for an air cleaner, there is known a filter in which a deodorizing filter made of a non-woven fabric formed with a carbon fiber and capable of effecting deodorization by the reaction of the carbon fiber with odor components in the air and of releasing the adsorbed odor components by heating at about 110° C. is shaped into a flat pouch and a plate-form heater having air permeability is enveloped in the pouch-like deodorizing filter to integrated them, but the filter has a problem in view of regeneration efficiency (cf. JP-A-10-332).

An object (purpose) of the invention relates to a deodorizing filter having a large capacity of deodorization performance and is to provide a thermally regenerative deodorizing filter which can be repeatedly used by conducting a thermal regeneration treatment.

SUMMARY OF THE INVENTION

The summary of at least one embodiment of the invention solving the above problems lies on the following.

A thermally regenerative deodorizing filter comprising:
a honeycomb base material of a deodorizing filter, which comprises at least a first kind of electroconductive sheet and a second kind of electroconductive sheet,
a deodorant packed in a cell of the honeycomb base material, and
a gas-permeable base material sealing openings at the both sides of the honeycomb base material,
wherein at least-one of said kinds of electroconductive sheets comprises a PTC heater and at least one of said kinds of electroconductive sheets does not comprise a PTC heater.

A thermally regenerative deodorizing filter, which comprises a honeycomb base material, a deodorant packed in a cell of the honeycomb base material, and a gas-permeable base material which seals openings at the both sides of the honeycomb base material,
wherein the honeycomb base material comprises a PTC heater,
the gas-permeable base material comprises an electroconductive material, and
the PTC heater is heated by applying a voltage between the gas-permeable base material.

BRIEF DESCRIPTION OF THE DRAWINGS

In FIGS. 1 to 9, 1 is a heating element, 2 is a deodorizing filter, 3 is a deodorant, 4 is a gas-permeable base material, 5 is an electroconductive sheet, 6 is a sheet-form PTC heater, each of 7 and 8 is a voltage applying part, 9 is a PTC heater, 10 is a gas-permeable base material, 11 is a deodorant, 12 is a crystalline macromolecular polymer, 13 is an electroconductive fine particle, and 14 is a tabular electrode.

DETAILED DESCRIPTION OF THE INVENTION

Figure 1:
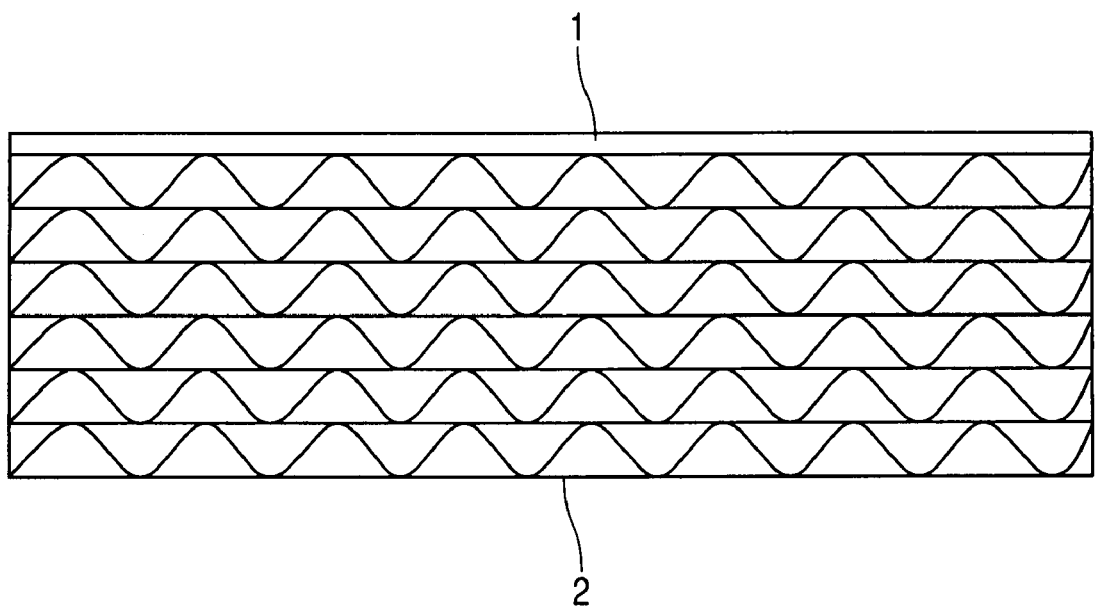
FIG. 1 is a drawing showing an example of a combination of a deodorizing filter and a heating element which are constituents of the thermally regenerative deodorizing filter of at least one embodiment of the invention.

The following will explain a first embodiment of the thermally regenerative deodorizing filter of the invention in detail.

Since the thermally regenerative deodorizing filter of at least one embodiment of the present invention is deodorized and regenerated efficiently by heating, it is specific that the part containing a deodorant has a honeycomb constitution. The constituents constituting the honeycomb base material, such as a thermally conductive material and a deodorant, preferably have heat resistance.

The honeycomb base material to be used in at least one embodiment of the invention is a structure comprising cell walls having openings, and a specific example of the honeycomb base material is a corrugated honeycomb obtainable by laminating single faced corrugated fiberboard manufactured in accordance with "exterior corrugated fiberboard" described in JIS-Z-16-1995, the honeycomb being described in JP-A-3-67644 or JP-A-5-338065.

A hexagon honeycomb composed of hexagonal cells, a honeycomb composed of square cells, a honeycomb composed of triangular cells, a honeycomb composed of hollow cylindrical cells, and the like, which are manufactured by the method may be mentioned.

The cell shape such as hexagon or square may be not only a regular polygon but also an irregular one with the rounded angle or the curved side.

The honeycomb base material according to the least one embodiment of the invention preferably possesses heat resistance and a honeycomb base material made of various thermally conductive materials having heat resistance, which is shaped by an adhesive having heat resistance to be mentioned below, can be employed.

The deodorant which is adaptable to thermal regeneration according to at least one embodiment of the invention is preferably a porous deodorant which is easy to regenerate by heating and should have heat resistance against the temperature of the heating element (PTC heater).

The material which can be used as the deodorant adaptable to the thermal regeneration according to at least one embodiment of the invention are the materials which are employed mainly for the purpose of removing offensive odors. Specifically, there may be used carbon-based adsorbing deodorant such as active carbon; for the purpose of strengthening deodorization performance against specific odor components, for example, active carbon impregnated with an amine-based substance for deodorization of aldehyde or a chemical agent such as an organic acid for deodorization of ammonia, active carbon fiber, bamboo charcoal and Bincho charcoal; an inorganic absorbing deodorant such as natural or synthetic zeolite (zeolite group), active alumina, an iron-based compound such as iron oxide, and porous silica; enzyme-based deodorant such as iron ascorbate or a phthalocyanine derivative of a metal such as iron, cobalt, or manganese; an oxidation catalyst such as a manganese-based oxide, a perovskite compound, platinum oxide, palladium oxide, or vanadium oxide; a composite of silicon carbide, silicon nitride, calcium silicate, aluminum oxide and silica; synthetic ceramic such as zirconia and far infrared ray ceramics such as heals stone or fergusonite, as well as, in the case that a temperature range of using the heating element is relatively low temperature, an organic adsorbing deodorant such as an organic acid-based compound, chitin, chitosan, and an ion exchange resin; a deodorant using a compound contained in a plant extract, such as catechin, tannin, flavonoid, limonen, or pinene plurality of these deodorants may be optionally used in combination or may be used as a hybrid deodorant by complexing these deodorants.

As the deodorant, particularly preferred is high-silica zeolite. Although, similar to usual zeolite, high-silica zeolite (hydrophobic zeolite) is a crystal of an aluminasilicate metal salt, the ratio of silica to alumina in the crystal is particularly high. Since the oxygen atom in the silica structure hardly has basicity and the Si—O—Si bond on the surface does not participate in the formation of hydrogen bonding, high-silica zeolite shows hydrophobicity and does not adsorb water molecules and hence it can effectively adsorb aldehydes and the like even under a highly humid environment and under a high temperature environment.

Furthermore, high-silica zeolite has a feature that it can adsorb a wide range of odorants including low-temperature compounds such as aldehydes which are generally difficult to remove by an adsorption method, for example, organic acids, ammonia, amines, ketones, sulfur-containing compounds such as hydrogen sulfide and mercaptans, indols and the like.

In addition, since it is excellent in adsorption of hydrophobic gases and neutral gases which are difficult to remove by regeneration with water washing, it is possible to complement the deodorization performance of a particulate deodorant which is suitable for regeneration with water washing, and thus the total deodorization can be achieved.

The honeycomb base material to be used in at least one embodiment of the invention is preferably any of alumina, silica, magnesium oxide, calcium oxide, nickel oxide, zinc oxide, titanium oxide, iron oxide, silicon carbide, titanium carbide, tantalum carbide, silicon nitride, aluminum nitride, boron nitride, beryllium oxide, silver, copper, aluminum, nickel, glass, graphite or a mixture thereof, as a material having a high thermal conductivity. The aforementioned oxides, carbides, and nitrides all have a heat conductivity of 10 W/m·k or more, and hence are suitable. Among them, particularly alumina, silica, zinc oxide, and silicon carbide are inexpensive and preferable.

These heat conductive materials may be used as an electroconductive sheet using a binder or may be supported on by surface treatment or the like of a sheet.

By using a heat conductive material, it becomes possible to transfer heat of the PTC sheet to the whole honeycomb effectively, and it results in improvement in thermal regeneration efficiency of the filter.

Although the heating element to be brought into contact with the heat conductive material in at least one embodiment of the invention is not necessarily subjected to insulation treatment, it is preferred for either the heat conductive base material or the heating element to have an insulating property.

In the case that the insulation treatment is performed, it is possible to use a material comprising an inorganic oxide, carbide, nitride, or the like or a material subjected to surface coating with a heat-resistant resin. As the surface coating agent, it is preferred to use a material which does not deactivate the performance of the deodorant to be supported.

As a method of supporting the deodorant on the honeycomb base material, the most convenient method may be a method of preparing a coating liquid in which the deodorant and a binder is dispersed after the formation of the honeycomb and then supporting it on the honeycomb surface by impregnation.

In addition, the supporting may be performed by a method of coating at a stage of sheet-form prior to processing into the honeycomb.

In this connection, since the binder to be used may cause deterioration of deodorization performance depending on the ratio thereof, it is preferred to restrict the ratio to not more than 60% of the total supporting weight.

The material of the heating element in at least one embodiment of the invention preferably comprises a heating body composed of either a ceramic heater or a linear heater made of tantalum, nichrome, or tungsten; or the heating body and a heat conductor.

As the heating element in at least one embodiment of the invention, there may be mentioned a heating body composed of either a ceramic heater or a linear heater made of tantalum, nichrome, or tungsten; or one having an electromicrowave generator, such as a microwave.

Among all, in view of easiness of ON/OFF switching and temperature control and simplicity of the structure, a heating body composed of a panel heater which tightly holds a linear heater composed of nichrome whose surface is subjected to insulation treatment, between two aluminum plates is preferred. There may be suitable a heating body in which heat of a heating heater selected from them is efficiently transferred to the deodorizing filter through the heat conductive material to effect heating.

With regard to the combining method of the heating element with the deodorizing filter, as an example of attachment is shown in FIG. 1, there is adopted a form wherein the heating element is tightly adhered to the honeycomb base material in a form of shaping an outer flame which is parallel to the deodorizing filter having a hollow tubular structure.

Specifically, the element is placed in a form of tightly adhered to a liner of the outer flame of the honeycomb base material or so as to come into contact with the inner core of the corrugate while playing a role of liner. Any manner may be suitable as far as heat of the heating element (heating heater) 1 is transferred to the deodorizing filter 2 by adopting this structure.

Figure 2:
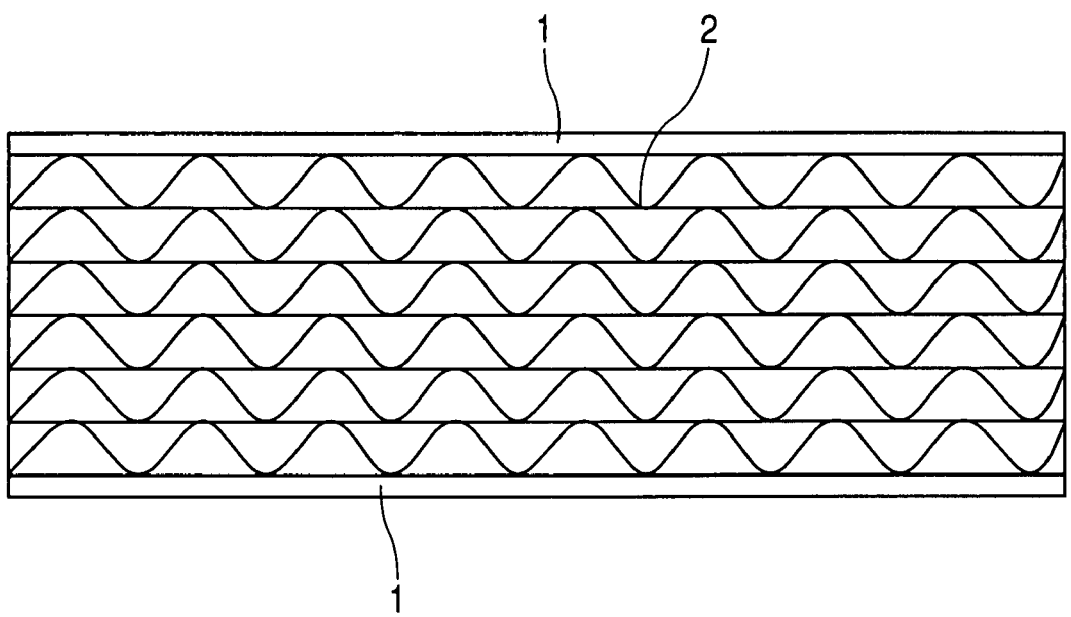
FIG. 2 is a drawing showing an example of a combination of a deodorizing filter and a heating heater which are constituents of the thermally regenerative deodorizing filter of at least one embodiment of the invention.
Figure 3:
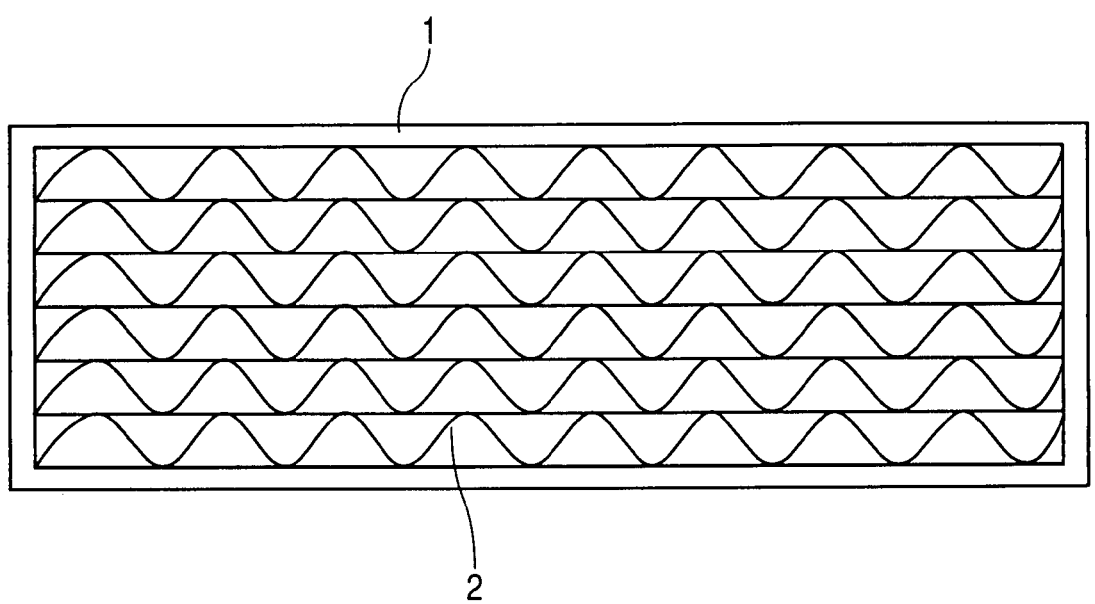
FIG. 3 is a drawing showing an example of a combination of a deodorizing filter and a heating element which are constitutive elements of the thermally regenerative deodorizing filter of at least one embodiment of the invention.
Figure 4:
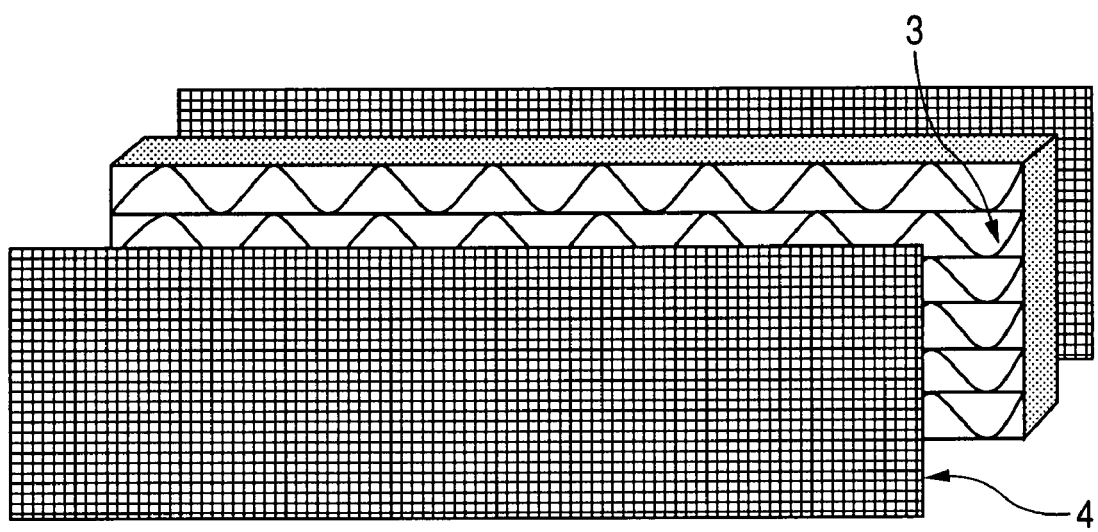
FIG. 4 is a drawing showing a whole constitution of the thermally regenerative deodorizing filter of at least one embodiment of the invention.

The heating element and the deodorizing filter is needed to be come into contact with each other at least one part. It is preferable to attach the heater to a plurality of sides at the circumference of the deodorizing filter as shown in FIG. 2, or to cover all the circumference of the deodorizing filter as shown in FIG. 3.

When an adhesive is used for the attachment of the heating element to the deodorizing filter, a heat-resistant adhesive which is sustainable to the temperature reachable by the heating element can be suitably selected and used. However, when the opening of the honeycomb is closed, a sufficient airflow is limited thereby, so that it is preferred to attach the heating element so as not to close the opening as far as possible.

As a heat-resistant adhesive to be preferably used, an ethylene-vinyl acetate copolymer, a polyamide, a polyester, or a synthetic rubber-based hot-melt adhesive is employed and, furthermore, there may be mentioned a styrene-butadiene-styrene triblock copolymer, a pre-condensate composed of N,N'-(4,4'-diphenylmethane)bismaleimide and 4,4'-diaminodiphenylmethane, a coumarone-indene resin and a terpene resin, an adhesive obtained by further blending a terpene-phenol resin thereto, or the like, but the heat-resistant adhesive is not particularly limited thereto as far as it is used in a state sustainable to heat of the heating heater.

Next, the following will describe a thermally regenerative deodorizing filter of a second embodiment of the invention in detail.

The thermally regenerative deodorizing filter is a thermally regenerative deodorizing filter aiming at efficient thermal regeneration by particularly using a temperature-controllable PTC heater as the heating element, and the constituents such as the heat-conductive base material, the deodorant, and the adhesive to be used for the thermally regenerative deodorizing filter preferably have heat resistance.

PTC to be used for the heating element in the thermally regenerative deodorizing filter in at least one embodiment of the invention is an abbreviated designation of standard nomenclature "Positive Temperature Coefficient", and a ceramic PTC heater comprising barium titanate ($BaTiO_3$) or vanadium oxide ($V_2O_3$) as a main component, or an organic PTC heater obtained by dispersing conductive particles of carbon black, a metal, or the like can be employed.

The ceramic PTC heater evolves heat when an electric current flows through the element at electrification, whereby the temperature elevates to Curie temperature. The PTC heater has a function that the ohmic value increases at around Curie temperature to reduce the electric current.

When the electric current is reduced, the temperature of the PTC is gradually lowered and then the electric current again flows to evolve heat. Thus, the PTC heater has a property that the temperature thereof is controlled at around set Curie temperature.

Figure 8:
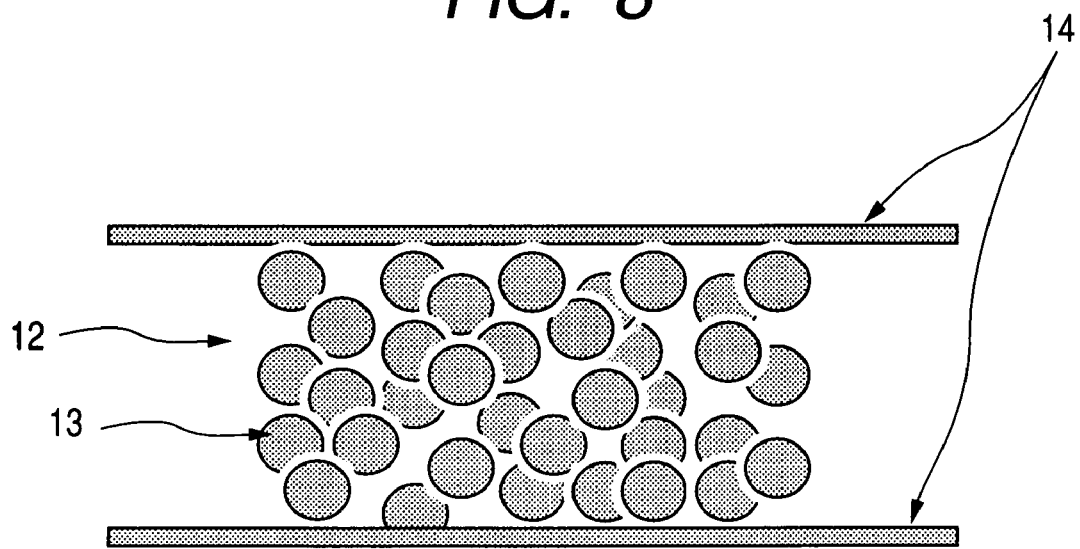
FIG. 8 is a drawing showing a low-temperature state of an organic PTC heater.

Moreover, the organic PTC heater is a heater in which a tabular electrode 14 is provided on the surface of a PTC heater element having a shaped constitution in which electroconductive particles 13 of carbon black, a metal, or the like are dispersed into a crystalline polymer 12, as shown in FIG. 8. Under a low-temperature condition, a myriad of electroconductive paths are present between respective electrodes and the resistance is low.

On this occasion, when a voltage is applied to the electrodes, an electric current flows and heat is evolved.

Figure 9:
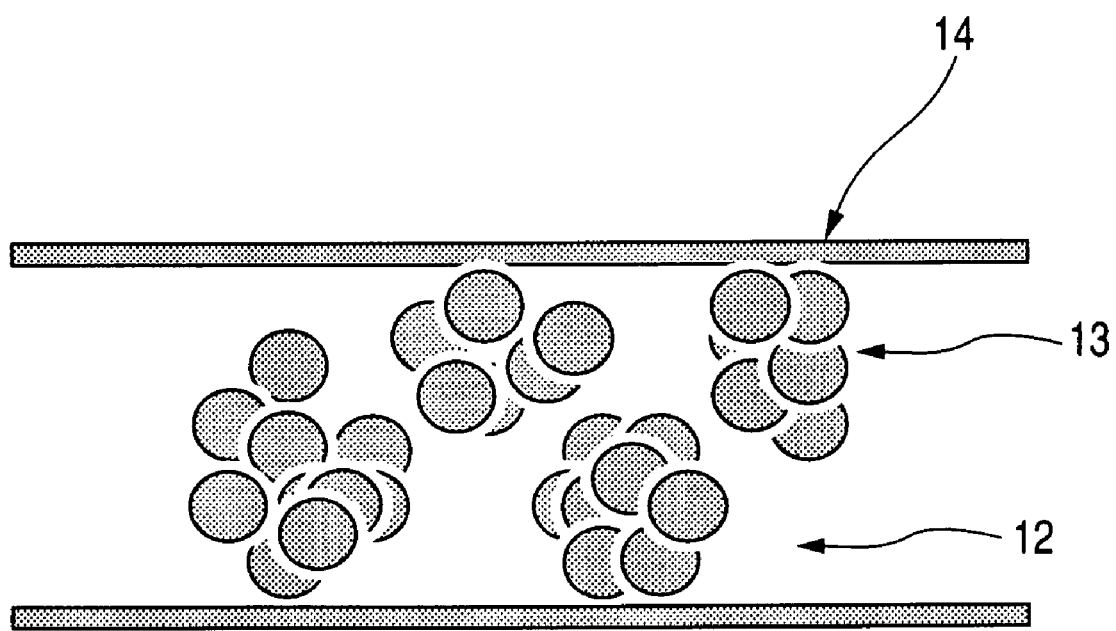
FIG. 9 is a drawing showing a high-temperature state of an organic PTC heater.

When the temperature reaches a temperature inherent to the material (in the present application, this temperature is expressed as a temperature corresponding to Curie temperature in the case of the ceramic one), as shown in FIG. 9, a dispersed state of the electroconductive particles becomes uneven by the thermal expansion of the crystalline polymer, and the electroconductive paths are broken to result in an increase of an ohmic value. Thus, electric current control and simultaneous temperature control become possible.

The inherent temperature can be freely set by changing the combination ratio of the crystalline polymer to the electroconductive particles.

In comparison with the ceramic PTC heater, the organic PTC heater has a low specific resistance at room temperature and hence is suitable for uses in which a large electric current is applied. Further, miniaturization is possible and the heater also possesses a self-controlling heater and temperature-detecting and overcurrent-protecting functions, so that it can be advantageously employed.

Examples of the polymer usable for the organic PTC heater include polyethylene, polyethylene oxide, t-4-polybutadiene, polyethylene acrylate, ethylne-ethyl acrylate copolymers, ethylene-acrylic acid copolymers, polyesters, polyamides, polyethers, polycaprolactam, fluorinated ethylene-propylene copolymer, chlorinated polyethylene, chlorosulfonated ethylene, ethylene-vinyl acetate copolymers, polypropylene, polystyrene, styrene-acrylonitrile copolymers, polyvinyl chloride, polycarbonate, polyacetal, polyalkylene oxide, polyphenylene oxide, polysulfone, fluorinated resins, and the like. At least one of these polymers may be used Specifically, they are suitably selected depending on the method of electrode formation, required properties of the PTC heater, and the like.

As preferred examples of the polymer, there may be mentioned polyethylene, Nylon 12, or polyethylene oxide PEO). Among these, when a relatively low Curie temperature of about 60 to 70° C. is targeted, polyethylene oxide or a mixture of high-density polyethylene and low-density polyethylene with a wax is preferred. In particular, for the purpose of lowering Curie temperature, preferred is a mixture of mixed polyethylene with a wax or polyethylene oxide.

As the electroconductive particles for use in the organic PTC heater, there may be mentioned Ni, Ti, Cu, Ag, Pd, Au, PT, and the like as metal particles, and particles of carbon black, Al2O3, TiO2, etc., with an Ag plating layer formed thereon; particles of BaTiO3 etc., with a Pd plating layer formed thereon; and the like as metal coating particles.

The organic PTC heater using carbon black as an electroconductive filler has been used as a overcurrent protecting element in large quantities. It is possible to lower the resistance of an organic PTC heater using atypical metal particles as the filler, which is currently actually used, to 1 mK2 or less (JP-A-5-47503).

The PTC heater using atypical metal particles as the filler is specific that it has an extremely small ohmic value and exhibits a large resistance-changing rate of 6 orders or more at a working temperature of 80° C. When the material having a large resistance-changing rate is used, it is possible to diminish the controllable width of temperature of the PTC element and highly accurate temperature control can be realized, so that high reliability is expected also from the practical viewpoint.

The Curie temperature of the PTC heater can be freely designed according to applications, and the Curie temperature of the PTC heater for use in at least one embodiment of the invention is preferably from 60 to 180° C.

This is because, although the deodorant for use in the thermally regenerative deodorizing filter is preferably porous zeolite or active carbon, for complete regeneration of these materials, a temperature of about 100° C. to 0° C. is sufficient and air-cleaning equipments are frequently controlled at a practical temperature of 100° C. or lower since they cannot mount a heat source reaching a high temperature of 100° C. or higher in many cases.

When the equipment is controlled at a temperature of 100° C. or lower, the regeneration rate sometimes do not reach 100%. However, the recovery of deodorization performance of 50% or more can be expected in many cases, when a temperature of about 60° C. is applied as the heating temperature.

The deodorant to be used in the thermally regenerative deodorizing filter of at least one embodiment of the invention preferably has a property of being regenerated at the heating temperature of the PTC heater used in at least one embodiment of the invention.

In the deodorant, although it is preferred to use a deodorant having the regenerating temperature close to the Curie temperature of the PTC heater, a PTC heater having Curie temperature lower than the regenerating temperature may be attached according to the designed principle of the deodorant.

Preferably, active carbon, high-silica zeolite, and the like can be recovered to initial deodorization performance by subjecting them to about 1 hour of heat treatment at 120° C.

The PTC heater to be used in the thermally regenerative deodorizing filter of at least one embodiment of the invention is attached so that heat of the heater can be efficiently transferred to the filter, and the position and the shape of the PTC heater are not limited as far as the whole deodorizing filter is heated through a heat conductive material.

Moreover, the following will describe a thermally regenerative deodorizing filter of a third embodiment of the invention.

Since the thermally regenerative deodorizing filter is regenerated by a PTC heater which is a heating element, the constituents such as the PTC sheet, the electroconductive sheet, the deodorant, and the adhesive constituting the thermally regenerative deodorizing filter preferably have heat resistance.

The honeycomb structural body to be used in the thermally regenerative deodorizing filter in this embodiment may be produced, for example, by laminating sequentially a single faced corrugated fiberboard in which inner core is bonded onto a liner to thereby manufacture a corrugated block and by cutting the corrugated block perpendicular to the liner surface thereof or at a certain angle obliquely to form a deodorizing filter of a corrugated honeycomb.

Moreover, with regard to a honeycomb filter having a square or hexagonal shape during the extension, a honeycomb filter is obtained by manufacturing a honeycomb block with steps of pasting to a constituting sheet in a plurality of lines at constant intervals, overlaying another constituting sheet thereon, pasting thereto in a plurality of lines at constant intervals with shifting the pitch, and further overlaying the other constituting sheet; cutting the block perpendicular to the paste line or with maintaining at a certain angle, and finally extending the cut block.

Namely, the thermally regenerative deodorizing filter of the third embodiment is constituted by packing a deodorant in the cells of a honeycomb base material and sealing both openings of the honeycomb base material with a gas-permeable base material, wherein the honeycomb base material comprises two or more electroconductive sheets and at least one of the electroconductive sheets is a self-temperature controlling PTC heater at electrification, and the other is composed of other electroconductive sheet(s). When the honeycomb base material is corrugated, it has a constitution of either a combination of an electroconductive sheet as the inner core part and a PTC sheet as the liner part or a combination of a PTC sheet as the inner core part, and an electroconductive sheet as the liner part, and thus becomes a structure in which PTC sheets are present between electroconductive sheets.

By applying a voltage to the both ends of the structure to send an electric current, the PTC sheet can be heated to Curie temperature.

Moreover, it may be constituted in a state in which both surfaces of the sheet-form PTC sheet are held between electroconductive electrode sheets, respectively. By sending an electric current to the electrode sheet, the electric current flows in the thickness direction of the PTC sheet, and hence the PTC sheet is evenly heated within a short period of time.

Furthermore, in order to heat the PTC sheet efficiently, the electroconductive base materials positioned at both sides of the PTC sheet should be independent from each other. When the base materials are short-circuited each other, the electric current does not flow through a PTC heater part having a high electric resistance and hence the heater does not evolve heat.

Therefore, when a gas-permeable sheet for sealing particulate active carbon is attached to the opening of the honeycomb base material, it is necessary to design the filter so as to achieve an electrically insulated state.

The PTC heater and the electroconductive sheet constituting the honeycomb base material of at least one embodiment of the invention preferably possess heat resistance, and there can be used a honeycomb base material which is shaped by using an adhesive having heat resistance to be mentioned below.

The electroconductive sheet to be used in the honeycomb base material of at least one embodiment of the invention is copper, aluminum, lead, nickel, chromium, titanium, gold, platinum, an iron oxide, graphite, or the like, and aluminum is particularly preferred.

In the case of using a metal sheet, a sheet having a thickness of 50 to 500 μm is used. These electroconductive sheets may be used with supporting a deodorant, a catalyst, or the like thereon, whereby the deodorization performance is further improved.

The electroconductive sheet to be used in at least one embodiment of the invention preferably has heat conductivity at the same time, and the heat conductive material is preferably any of alumina, silica, magnesium oxide, calcium oxide, nickel oxide, zinc oxide, titanium oxide, iron oxide, silicon carbide, titanium carbide, tantalum carbide, silicon nitride, aluminum nitride, boron nitride, beryllium oxide, silver, copper, aluminum, nickel, glass, and graphite or a mixture thereof. The aforementioned oxides, carbides, and nitrides all have a heat conductivity of 10 W/m·K or more and hence are suitable. Among all, particularly alumina, silica, zinc oxide, and silicon carbide are inexpensive and preferable.

These heat conductive materials may be used as an electroconductive sheet using a binder or may be supported on by surface treatment or the like of a sheet.

By using a heat conductive material, it becomes possible to transfer heat of the PTC sheet to the whole honeycomb effectively, and it results in improvement in thermal regeneration efficiency of the filter.

The particulate deodorant according to at least one embodiment of the invention is a particulate deodorant and the size of the particle may be large enough so as not to fall out of the mesh of the gas-permeable base material used for sealing and also storable in the cells of the honeycomb.

The shape of the particulate deodorant according to at least one embodiment of the invention is not particularly limited and may be spherical, tetrahedral, hexahedral, octahedral, cylindrical, polygonal-columnar shape, rod-like, plate-like one, or the like.

Among these, a hollow columnar or tubular shape, or a concave polygonal columnar shape such as a star shape or a gear shape, or the like shape is advantageous for deodorization since the surface area of the particulate deodorant increases, and is also advantageous for gas permeation since flow path of air can be secured in the cells of the honeycomb base material.

As a method for manufacturing the particulate deodorant according to at least one embodiment of the invention, there may be mentioned a method of shaping a powdery deodorant into particles using any of various granulators such as an extrusion granulator, a stirring granulator, a fluidizing granulator, a rolling granulator, a compression granulator, or a tableting machine, and a method of crushing a clumpy deodorant into particles using any of dry or wet crushing machines such as a ball mill, a vibration mill, a roll mill, a centrifugal mill, or a jet mill. The resulting particulate deodorant can be regulated to a desired particle size using any of various classification methods such as sieving type and cyclone type.

The deodorant according to at least one embodiment of the invention preferably has heat resistance against Curie temperature of the PTC sheet and is preferably capable of regenerating the deodorizing power of the thermally regenerative deodorizing filter by the heat of the PTC sheet.

The material usable as such a deodorant is a material which is employed mainly for the purpose of removing offensive smells. Specifically, there may be mentioned a carbon-based adsorbing deodorant such as active carbon, impregnated active carbon, active carbon fiber, bamboo charcoal, and Bincho charcoal; an inorganic absorbing deodorant such as natural and synthetic zeolite (zeolite group), active alumina, an iron-based compound such as iron oxide, and porous silica; an organic adsorbing deodorant such as an organic acid-based compound, chitin, chitosan, or an ion exchange resin; an enzyme-based deodorant such as iron ascorbate and a phthalocyanine derivative of a metal such as iron, cobalt, or manganese; an oxidation catalyst such as a manganese-based oxide, a perovskite compound, platinum oxide, palladium oxide, or vanadium oxide; silicon carbide; silicon nitride; calcium silicate; alumina-silica; a synthetic ceramic such as zirconia or a far infrared ray ceramic such as heals stone or fergusonite; or a deodorant using a compound contained in a plant extract, such as catechin, tannin, flavonoid, limonen, or pinene.

A plurality of these deodorants may be optionally used in combination, if necessary, or may be used as a hybrid deodorant by complexing these deodorants.

At that occasion, it is preferred to use the deodorant after granulation with a heat-resistant binder.

The sealing of the particulate deodorant according to at least one embodiment of the invention is performed by holding both openings of the honeycomb, in which the particulate deodorant is packed, between two sheets of a gas-permeable base material, and the main purpose of the sealing is the prevention of falling of the particulate deodorant.

As the specific methods of sealing, a method of adhering the gas-permeable material to the end of the cell wall of the honeycomb base material, a method of fixing the honeycomb base material and the gas-permeable material in the process of attaching the frame, and the like may be mentioned.

As the gas-permeable base material, in addition to woven fabrics, dry unwoven fabrics, melt-blown nonwoven fabrics, spun-bond nonwoven fabrics, air-laid pulp, wet nonwoven fabrics, various papers, nets, honeycombs, foams, sponges, felts, and the like, there may be mentioned sheets having a large number of holes made in general-purpose resin films and thin plates such as polyethylene film, polypropylene film, and polyester films, as well as metal nets and the like.

In the case of using a metal net, however, it must be arranged so that it is electrically insulated from the honeycomb part.

The gas-permeable base material according to at least one embodiment of the invention may possess functions of deodorization, dust removal, antibacterial ability, insect proofing ability, insect repellency, and the like unless it deviates the gist of the at least one embodiment of the invention.

Figure 5:
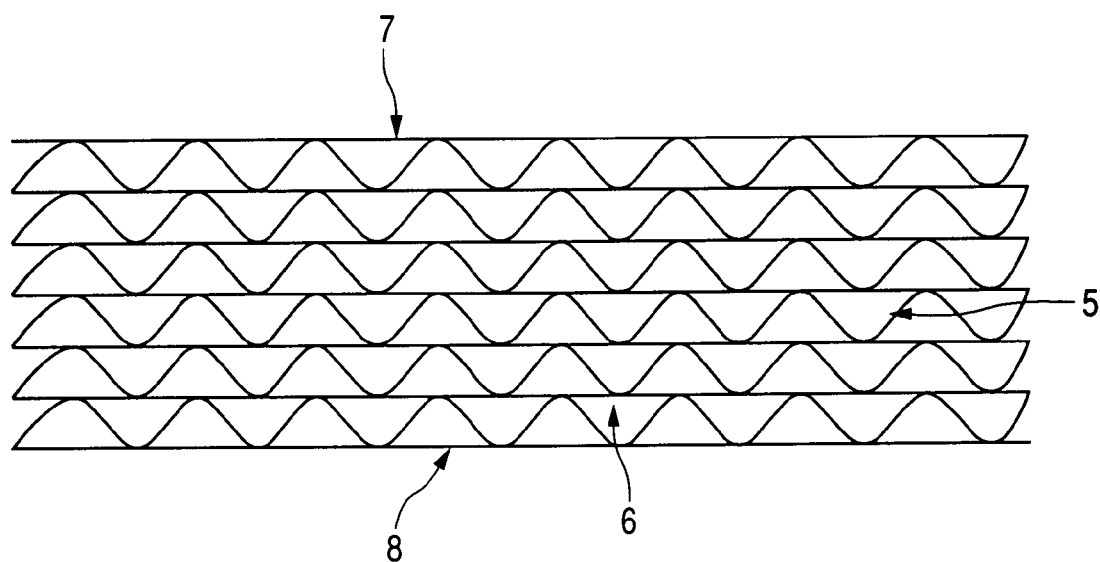
FIG. 5 is a drawing showing an example of an arrangement of an electroconductive sheet and a sheet-form PTC heater which are corrugated constituents of at least one embodiment of the invention.
Figure 6:
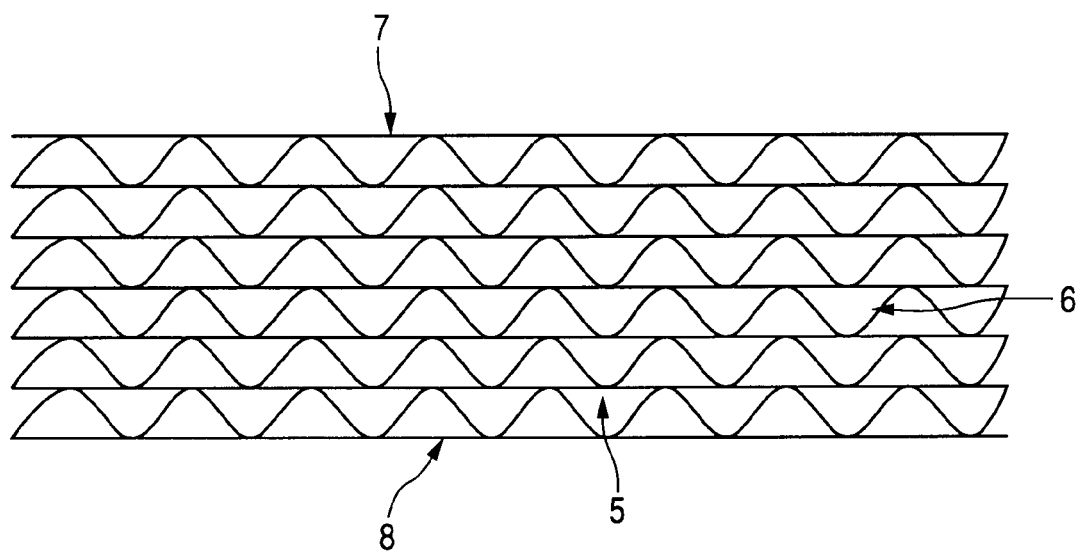
FIG. 6 is a drawing showing an example of an arrangement of an electroconductive sheet and a sheet-form PTC heater which are corrugated constituents of at least one embodiment of the invention.

As the arranging method of the PTC heater to the deodorizing filter, an electroconductive sheet (5) is arranged at the inner core part and a sheet-form PTC heater (6) at the liner part regularly as in FIG. 5 or a sheet-form PTC heater (6) is arranged at the inner core part and an electroconductive sheet (5) at the liner part regularly as in FIG. 6, as shown in the explanatory drawing in detail, and they must have a constitution capable of applying a voltage so that an electric current flows one liner to the other of the liner parts (7, 8) at the both ends.

In particular, as shown in FIG. 5, when the sheet-form PTC heater is placed at the liner part, since the voltage-applying terminal and the PTC come into direct contact with each other, it is preferable to use an electroconductive sheet as the liner parts (7, 8).

When an adhesive is used in the arrangement of the PTC heater, a heat-resistant binder sustainable to the maximum temperature of the heating element can be suitably selected and used.

Moreover, the following will describe a heat regenerative deodorant filter of a fourth embodiment of the invention in detail.

Figure 7:
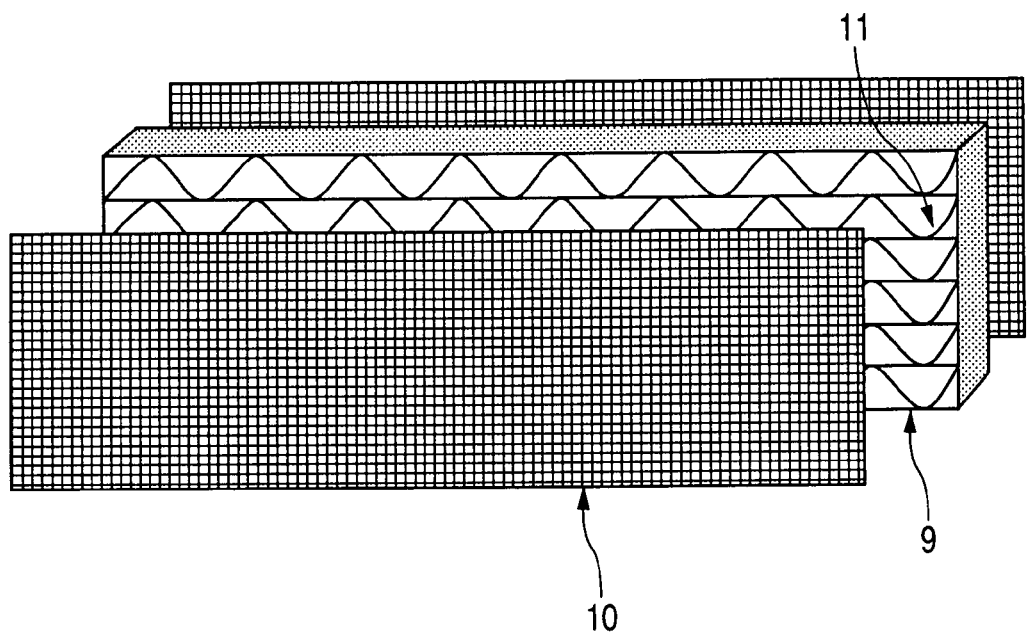
FIG. 7 is a drawing showing a whole constitution of the thermally regenerative deodorizing filter of at least one embodiment of the invention.

The constitution of the heat regenerative deodorant filter of at least one embodiment of the invention is shown in FIG. 7. The heat regenerative deodorant filter of at least one embodiment of the invention has a structure in which a particulate deodorant 11 is packed in cells of a honeycomb base material containing a PTC heater 9 and both openings of the honeycomb base material are sealed with a gas-permeable base material 10 having electroconductivity so that the particulate deodorant is not scattered and lost. Then, by electrification from the gas-permeable base material 10 at the both openings, the PTC heater evolves heat and the sealed particulate deodorant 11 is regenerated by the heat.

In that case, the constitutive materials of the honeycomb base material other than the PTC should be insulators. This is because the PTC is not electrified to be heated, when an electroconductive material is used as an element other than the PTC.

Therefore, the PTC heater, the gas-permeable base material possessing electroconductivity, the deodorant, and the adhesive used according to necessity, which constitute the heat regenerative deodorant filter preferably have heat resistance against Curie temperature of the PTC heater.

Namely, the heat regenerative deodorant filter of at least one embodiment of the invention has characteristics that the honeycomb base material is constituted including part of the PTC heater, the PTC heater is electrically connected with the electroconductive gas-permeable base material to be used for sealing the deodorant inside the honeycomb, and the deodorization performance of the sealed deodorant is regenerated by applying a voltage to the gas-permeable base material to heat the honeycomb base material.

When a material other than the PTC is used as a constitutive material of the honeycomb base material, an insulating material is used.

The gas-permeable base material to be used for the sealing and the honeycomb base material are preferably combined with each other in a tightly adhered state, and more preferably, a large number of contact points are present between the gas-permeable base material and the honeycomb base material.

This is because the presence of a large number of the contact points can result in increasing heating efficiency. In the case of a small number of the contact points, the electric current may flow only through paths having a low ohmic value, so that it takes longer time and larger electricity to heat the whole honeycomb base material.

Moreover, the gas-permeable base materials provided at both sides of the honeycomb base material are placed independently from each other through the honeycomb base material. When both gas-permeable base materials come into contact with each other and short-circuited, a path having a low electric resistance which does not pass through the PTC heater is formed and the PTC heater does not evolve heat, so that the case is, as a matter of course, not preferred.

The PTC heater constituting the honeycomb base material according to at least one embodiment of the invention preferably possesses heat resistance and an adhesive having heat resistance to be mentioned below can be used for shaping a honeycomb base material and also for adhering the gas-permeable base material possessing electroconductivity and the honeycomb.

PREPARATION EXAMPLE 1

A hexagonal honeycomb having a cell size of 10 mm and an outside size of 100 mm×200 mm×10 mm was prepared using an aluminum sheet possessing heat conductivity. This honeycomb was immersed into a coating liquid in which 80% by weight of high-silica zeolite and 20% by weight of an ethylene-vinyl acetate binder possessing heat resistance were dispersed so that the total concentration of solid matter was 30% by weight, whereby a deodorizing filter of Preparation Example 1 was formed. The high-silica zeolite was supported in a weight of 10 g on the deodorizing filter of Preparation Example 1.

PREPARATION EXAMPLE 2

A corrugated honeycomb having a pitch of 10 mm, a step height of 9 mm, and an outside size of 100 mm×200 mm 20×10 mm was prepared using an aluminum sheet possessing heat conductivity. This honeycomb was immersed into a coating liquid in which 80% by weight of coconut husk active carbon and 20% by weight of an ethylene-vinyl acetate binder possessing heat resistance were dispersed so that the total concentration of solid matter was 30% by weight, whereby a deodorizing filter of Preparation Example 2 was formed.

The high-silica zeolite was supported in a weight of 10 g on the deodorizing filter of Preparation Example 2.

PREPARATION EXAMPLE 3

A deodorizing filter of Preparative Example 3 was formed in the same manner as in Preparation Example 1 except that a nonwoven sheet having a basic weight of 100 g/m² and low heat conductivity, which comprises a polyester fiber and an acrylic fiber as main fibers, is used instead of the aluminum sheet possessing heat conductivity of Preparation Example 1.

PREPARATION EXAMPLE 4

A deodorizing filter of Preparative Example 4 was formed in the same manner as in Preparation Example 2 except that a nonwoven sheet having a basic weight of 100 g/m² and low heat conductivity, which comprises a polyester fiber and an acrylic fiber as main fibers, is used instead of the aluminum sheet possessing heat conductivity of Preparation Example 2.

PREPARATION EXAMPLE 5

A corrugate comprising an aluminum sheet having a thickness of 0.2 mm as an inner core part and a PTC sheet having a thickness of 0.2 mm and Curie temperature of 100° C. as a liner part was prepared with a size of 200 mm×100 mm×10 mm, a pitch of 10 mm, and a height of 8.5 mm, the corrugate being a honeycomb base material of Preparation Example 5.

PREPARATION EXAMPLE 6

A corrugate comprising an aluminum sheet having a thickness of 0.2 mm as a liner part and a PTC sheet having a thickness of 0.2 mm and Curie temperature of 100° C. as an inner core part was prepared with a size of 200 mm×100 mm 10×10 mm, a pitch of 10 mm, and a height of 8.5 mm, the corrugate being a honeycomb base material of Preparation Example 6.

PREPARATION EXAMPLE 7

A honeycomb having a pitch of 12 mm, a height of 10 mm, a size of 200 mm×100 mm×10 mm was prepared using a sheet-form PTC heater having a thickness of 0.2 mm and Curie temperature of 100° C. as a honeycomb base material, the honeycomb being a honeycomb base material of Preparation Example 7.

PREPARATION EXAMPLE 8

A honeycomb having a size of 200 mm×100 mm×10 mm, a pitch of 12 mm, and a height of 10 mm was prepared using, as a honeycomb base material, a sheet-form PTC heater having Curie temperature of 100° C., which is obtainable by homogeneously supporting a PTC material containing barium titanate on an insulating wet-type nonwoven fabric sheet having a thickness of 0.2 mm, the honeycomb being a honeycomb base material of Preparation Example 8.

EXAMPLE 1

A heating heater comprising a panel heater in which a linear heater made of a surface-insulated nichrome had been held between aluminum plates was bonded to the circumference of the deodorizing filter of Preparation Example 1 with an ethylene-vinyl acetate copolymer adhesive having a heat resistance to form a thermally regenerative deodorizing filter of Example 1.

EXAMPLE 2

A heating heater comprising a panel heater in which a linear heater made of a surface-insulated nichrome had been held between aluminum plates was bonded to the circumference of the deodorizing filter of Preparation Example 2 with an ethylene-vinyl acetate copolymer adhesive having a heat resistance to form a thermally regenerative deodorizing filter of Example 2.

EXAMPLE 3

A heating heater comprising a panel heater in which a linear heater made of nichrome had been held between aluminum plates was bonded to only one side of the long side parts in the circumference of the deodorizing filter of Preparation Example 2 with an ethylene-vinyl acetate copolymer adhesive having a heat resistance to form a thermally regenerative deodorizing filter of Example 3.

EXAMPLE 4

A PTC heater having Curie temperature of 100° C. was bonded to the circumference of the deodorizing filter of Preparation Example 1 with an ethylene-vinyl acetate copolymer adhesive having a heat resistance to form a thermally regenerative deodorizing filter of Example 4.

EXAMPLE 5

A PTC heater having Curie temperature of 100° C. was bonded to the circumference of the deodorizing filter of Preparation Example 2 with an ethylene-vinyl acetate copolymer adhesive having a heat resistance to form a thermally regenerative deodorizing filter of Example 5.

EXAMPLE 6

A particulate high-silica zeolite was included in the honeycomb base material of Preparation Example 5 in an amount of 50 g and both openings of the honeycomb base material were sealed with a stainless steel net insulated with a heat-resistant resin coating as an gas-permeable base material to prepare a deodorizing filter. Then, an aluminum plate fitted with a terminal for applying a voltage was attached to the liner parts of both sides of the honeycomb base material to form a thermally regenerative deodorizing filter of Example 6.

EXAMPLE 7

A particulate high-silica zeolite was included in the honeycomb base material of Preparation Example 6 in an amount of 50 g and both openings of the honeycomb base material were sealed with a stainless steel net insulated with a heat-resistant resin coating as an gas-permeable base material to prepare a deodorizing filter. Then, an aluminum plate fitted with a terminal for applying a voltage was attached to the liner parts of both sides of the honeycomb base material to form a thermally regenerative deodorizing filter of Example 7.

EXAMPLE 8

A particulate high-silica zeolite was included in the honeycomb base material of Preparation Example 7 in an amount of 50 g and both openings of the honeycomb base material were sealed with an gas-permeable electroconductive stainless steel net to prepare a deodorizing filter. A terminal for applying a voltage was attached to the gas-permeable materials at both sides to form a thermally regenerative deodorizing filter of Example 8.

EXAMPLE 9

A particulate active carbon was included in the honeycomb base material of Preparation Example 8 in an amount of 50 g and both openings of the honeycomb base material were sealed with an gas-permeable aluminum net to prepare a deodorizing filter. A terminal for applying a voltage was attached to the aluminum nets at both sides to form a thermally regenerative deodorizing filter of Example 9.

COMPARATIVE EXAMPLE 1

A heating element comprising a panel heater in which a heating heater made of nichrome had been held between insulated aluminum plates was bonded to the circumference of the deodorizing filter of Preparation Example 3 with an ethylene-vinyl acetate copolymer adhesive having a heat resistance to form a thermally regenerative deodorizing filter of Comparative Example 1.

COMPARATIVE EXAMPLE 2

A heating heater comprising a panel heater in which a heating element made of nichrome had been held between insulated aluminum plates was bonded to only one side of the long side parts in the circumference of the deodorizing filter of Preparation Example 4 with an ethylene-vinyl acetate copolymer adhesive having a heat resistance to form a thermally regenerative deodorizing filter of Comparative Example 2.

COMPARATIVE EXAMPLE 3

A heating element comprising a panel heater in which a heating heater made of nichrome had been held between insulated aluminum plates was placed around the circumference of the deodorizing filter of Preparation Example 1 with a space of 10 mm to form a thermally regenerative deodorizing filter of Comparative Example 3.

COMPARATIVE EXAMPLE 4

A particulate high-silica zeolite was packed in the cells of the honeycomb base material of Preparation Example 5 in an amount of 50 g, and one opening of the corrugate was sealed with a urethane foam as an gas-permeable material and another opening of the honeycomb base material was sealed with a spunbond nonwoven fabric as an gas-permeable base material to prepare a deodorizing filter, which was used as a water-washing regenerative deodorizing filter of Comparative Example 4.

COMPARATIVE EXAMPLE 5

A particulate high-silica zeolite was packed in the cells of the honeycomb base material of Preparation Example 5 in an amount of 50 g, and both openings of the honeycomb base material was sealed with a spunbond nonwoven fabric as an gas-permeable base material to prepare a deodorizing filter, which was used as a water-washing regenerative deodorizing filter of Comparative Example 5.

COMPARATIVE EXAMPLE 6

A particulate high-silica zeolite was packed in the cells of the honeycomb base material of Preparation Example 7 in an amount of 50 g, and one opening of the honeycomb was sealed with a urethane foam as an gas-permeable material and another opening of the honeycomb was sealed with a spunbond nonwoven fabric as an gas-permeable base material to prepare a deodorizing filter, which was used as a water-washing regenerative deodorizing filter of Comparative Example 6.

COMPARATIVE EXAMPLE 7

A particulate high-silica zeolite was packed in the cells of the honeycomb base material of Preparation Example 7 in an amount of 50 g, and both openings of the honeycomb was sealed with a spunbond nonwoven fabric as an gas-permeable base material to prepare a deodorizing filter, which was used as a water-washing regenerative deodorizing filter of Comparative Example 7.

COMPARATIVE EXAMPLE 8

A particulate active carbon as an adsorbent having electroconductivity was packed in the cells of the honeycomb base material made of a nonwoven fabric having an insulating property in an amount of 50 g and both openings of the honeycomb base material was sealed with a stainless steel net which was gas-permeable and has electroconductivity to form a deodorizing filter of Comparative Example 8 having a structure in which the stainless steel net is electrified to thereby cause heat evolution by PTC.

The following will show evaluation methods and evaluation results illustrating superiority of the first embodiment of the invention and will describe specific advantages of the first embodiment of the invention.

Acetaldehyde Deodorization Performance Test

Each of the thermally regenerative deodorizing filter of Examples 1 to 3 and Comparative Examples 1 to 3 was mounted on an air cleaner for test. While the cleaner was operated in a closed vessel of 1 m$^3$, acetaldehyde standard gas was gradually injected thereinto and the volume W (ml) of acetaldehyde injected was determined until the acetaldehyde concentration in the closed vessel detected using a gas detecting tube reached 20 ppm.

Then, each of the thermally regenerative deodorizing filter of Examples and Comparative Examples was subjected to regeneration treatment by the method to be mentioned below. Thereafter, the deodorizing test was again carried out in the same manner as above to determine the volume X (ml) of acetaldehyde injected.

A value (X/W) obtained by dividing the volume of acetaldehyde gas injected after regeneration by the initial volume of acetaldehyde gas injected was determined to be defined as a thermal regeneration efficiency (%).

Regeneration Treatment

After the volume W (ml) of acetaldehyde was determined, the heating heater was switched ON and heating treatment was carried out for minutes. After 15 minutes, the temperature of the heating heater was 230° C.

A test was conducted by the above method. The results of evaluating the performance are shown in Table 1.

TABLE 1

| Example or Comparative Example | Thermal regeneration efficiency (%) |
| --- | --- |
| Example 1 | 106% |
| Example 2 | 103% |

TABLE 1-continued

| Example or Comparative Example | Thermal regeneration efficiency (%) |
|---|---|
| Example 3 | 105% |
| Comparative Example 1 | 42% |
| Comparative Example 2 | 8% |
| Comparative Example 3 | 12% |

From the results shown in Table 1, it is understood that a high thermal regeneration efficiency is obtained since the thermally regenerative deodorizing filters of at least one embodiment of the invention can efficiently transfer the heat of the heating element brought into contact with the deodorizing filter.

On the other hand, it is understood that the thermally regenerative deodorizing filters shown in Comparative Examples cannot efficiently transfer the heat of the heating element and hardly regenerated since they use a nonwoven fabric having a low heat conductivity or the heating element does not come into contact with the deodorizing filter.

In particular, a filter using active carbon like the thermally regenerative deodorizing filter of Comparative Example 2 requires heat of 100° C. or higher for its regeneration and is hardly regenerated at a low temperature, but this disadvantage can be overcome by the use of a heat conductive base material as in the case of the thermally regenerative deodorizing filter of Example 2.

Furthermore, in the thermally regenerative deodorizing filter of at least one embodiment of the invention, since the odors entrapped in the deodorant are completely removed by thermal regeneration, it is understood that a higher deodorization efficiency is obtained in comparison with the initial deodorization performance.

This fact means that the deodorizing filter immediately after its preparation has entrapped a minute amount of organic compounds generated from the binder and the like and odors in the air, and hence is in a slightly deteriorated state in performance.

According to at least one embodiment of the invention, there is obtained a thermally regenerative deodorizing filter having a large deodorization capacity and usable for repeated deodorization by efficiently transferring the heat of the bonded heating element to the heat conductive deodorizing filter after use.

The following will show evaluation methods and evaluation results illustrating superiority of the second embodiment of the invention and will describe specific advantages of the second embodiment of the invention.

Acetaldehyde Deodorization Performance Test

Each of the thermally regenerative deodorizing filter of Examples 1, 2, 4, and 5 was mounted on an air cleaner for test. While the cleaner was operated in a closed vessel of 1 m³, acetaldehyde standard gas was gradually injected thereinto and the volume W (ml) of acetaldehyde injected was determined until the acetaldehyde concentration in the closed vessel detected using a gas detecting tube reached 20 ppm.

Then, each test body was subjected to regeneration treatment by the method to be mentioned below. Thereafter, the deodorizing test was again carried out in the same manner as above to determine the volume X (ml) of acetaldehyde injected.

A value (X/W) obtained by dividing the volume of acetaldehyde gas injected after regeneration by the initial volume of acetaldehyde gas injected was determined and was defined as a thermal regeneration efficiency (%).

Regeneration Treatment A

After the volume W (ml) of acetaldehyde was determined, the heating heater was switched ON and heating treatment was carried out for minutes.

Regeneration Treatment B

After the volume W (ml) of acetaldehyde was determined, the heating heater was switched ON and heating treatment was carried out for 20 minutes.

Shape Test

On each test body subjected to thermal regenerative treatment at Regeneration treatment B, shape distortion was evaluated visually according to the following standard.

Evaluation Level

◉: No change is observed before test.

○: Slight distortion is observed.

Δ: Shape distortion and exfoliation at adhered part are observed.

X: Structure cannot be maintained.

A test was conducted by the above method. The results of evaluating the performance are shown in Table 2.

TABLE 2

| Example or Comparative Example | Thermal regeneration efficiency A ($) (Regeneration treatment A) | Thermal regeneration efficiency B (%) (Regeneration treatment B) | Shape test result |
|---|---|---|---|
| Example 1 | 102 | 78 | ○ |
| Example 2 | 104 | 73 | Δ |
| Example 4 | 103 | 104 | ◎ |
| Example 5 | 101 | 101 | ◎ |

From the results shown in Table 2, since the heat of the heating element brought into contact with the deodorant filter is efficiently transferred to the deodorizing filter and contributes to regeneration in the thermally regenerative deodorizing filters of at least one embodiment of the invention, a high deodorization efficiency was obtained in any of Examples 1, 2, 4, and 5 in the case of Regeneration treatment A.

However, the deodorizing filters of Examples 1 and 2 exhibited a low value in the case of Regeneration treatment B. This result may be explainable as follows: since the regeneration treatment was carried out for a long period of 120 minutes, the adhesive part was carbonized into gases and the filter itself adsorbed these combustion gases, whereby the deodorization efficiency was lowered.

On the other hand, the thermally regenerative deodorizing filters of Examples 4 and 5 according to the second embodiment maintain a constant temperature of 100° C. which is Curie temperature thereof, and hence such an influence is not observed. This tendency is remarkable from the results of the shape test. When heated for a long time in a state without temperature controlling function like a nichrome linear heater, the temperature increased temperature was transferred to the deodorizing filter, that the adhesive used for the honeycomb base material and the adhesive used at the attached part between the heater and the deodorizing filter were carbonized and embrittled to cause exfoliation, falling of the heater, and the like.

In the test bodies of Examples 1 and 2 in which a nichrome linear heater was used, the temperature of the heater part after 120 minutes reached a high temperature near to 300° C.

Usually, heat of about 100° C. to 150° C. is necessary for complete regeneration of the deodorization performance of the deodorant. However, there is a risk that the surface conditions of the deodorant is modified to lower the deodorization performance and the binder or the like used in combination are thermally decomposed to generate decomposition gases which deteriorates the performance, and the filter itself is burned and carbonized under an excessively high temperature condition, so that the condition is not preferred.

As an element to be built in various air-conditioning equipments, the test bodies such as those of Examples 1 and 2, which is for example an element such as the nichrome linear heater elevating the temperature to a high temperature and difficult to control are not suitable, also from the viewpoint of safe use of a filter.

The use of the thermally regenerative deodorizing filter of the second embodiment enables repeated use any number of times, and it is possible to use it safely without risk of combustion and ignition even at heating over a long period of time.

According to the at least one embodiment of the invention, there is obtained a thermally regenerative deodorizing filter having a large deodorization capacity and usable safely for repeated deodorization over a long period of time, since the combined PTC heater controls temperature at a constant temperature after use.

The following will show evaluation methods and evaluation results illustrating superiority of the third embodiment of the invention and will describe specific advantages of the third embodiment of the invention.

Ammonia Deodorization Performance Test

Each of the thermally regenerative deodorizing filter of Examples 6 and 7 and Comparative Examples 4 and 5 was mounted on an air cleaner for test. While the cleaner was operated in a closed vessel of 1 m$^3$, ammonia standard gas was gradually injected thereinto and the volume W (ml) of ammonia injected was determined until the ammonia concentration in the closed vessel detected using an ammonia gas sensor reached 20 ppm.

Then, each of the deodorizing filter of Examples and Comparative Examples was subjected to regeneration treatment by the method to be mentioned below. Thereafter, the deodorization test was again carried out in the same manner as above to determine the volume X (ml) of acetaldehyde injected.

A value (X/W) obtained by dividing the volume of ammonia gas injected after regeneration by the initial volume of ammonia gas injected was determined and was defined as an ammonia-deodorizing regeneration rate (%).

Acetaldehyde Deodorization Performance Test

Each of the thermally regenerative deodorizing filter of Examples 6 and 7 and Comparative Examples 4 and 5 was mounted on an air cleaner for test. While the cleaner was operated in a closed vessel of 1 m$^3$, acetaldehyde standard gas was gradually injected thereinto and the volume Y (ml) of acetaldehyde injected was determined until the acetaldehyde concentration in the closed vessel detected using a VOC sensor reached 5 ppm.

Then, each of the deodorizing filters of Examples 6 and 7 and Comparative Examples 4 and 5 was subjected to regeneration treatment by the method to be mentioned below. Thereafter, the deodorizing test was again carried out in the same manner as above to determine the volume Z (ml) of acetaldehyde injected.

A value (Z/Y) obtained by dividing the volume of acetaldehyde gas injected after regeneration by the initial volume of acetaldehyde gas injected was determined and was defined as an aldehyde-deodorizing regeneration rate (%).

Regeneration Treatment (Thermal Regeneration)

On the test bodies of Examples 6 and 7, after the test was finished in the ammonia deodorization performance test and in the aldehyde deodorization performance test, a voltage was applied to the terminals attached to the end of each honeycomb to evolve heat on the PTC sheet, whereby regeneration treatment was carried out under 180 minutes heating.

After the thermal regeneration, the test bodies were allowed to stand until the temperature thereof became to a room temperature.

Regeneration Treatment (Water-Washing Regeneration)

On the test bodies of Comparative Examples 4 and 5, in the ammonia deodorization performance test or in the of aldehyde deodorization performance test, the deodorizing filters of examples and Comparative Examples used for the first measurement were individually immersed for 1 hour in an aqueous solution in which a standard amount of a commercially available household neutral detergent (trade name "Mamalemon", manufactured by Lion Corporation.) was further diluted 10 times, then thoroughly rinsed by immersion for 1 hour while introducing tap water, and dried in the sun for 8 hours after draining off the water, whereby treatment for regenerating the deodorizing ability was carried out.

Shape Test

On each test body subjected to thermal regenerative treatment repeated 10 times, shape distortion was evaluated visually according to the following standard.

Evaluation Level

⊚: No change is observed before test.

○: Slight distortion is observed.

Δ: Shape distortion and exfoliation at adhered part are observed.

X: Structure cannot be maintained.

A test was conducted by the above method. The results of evaluating the performance are shown in Table 3.

TABLE 3

| Example or Comparative Example | Aldehyde deodorization test (%) | Ammonia deodorization test (%) | Shape test |
|---|---|---|---|
| Example 6 | 101 | 98 | ⊚ |
| Example 7 | 100 | 97 | ⊚ |
| Comparative Example 4 | 56 | 67 | Δ |
| Comparative Example 5 | 53 | 65 | ○ |

From the results of Table 3, it is understood that a regeneration efficiency of nearly 100% is obtained for both of aldehyde and ammonia, when the thermally regenerative deodorizing filters of Examples 6 and 7 which are practical examples of the third embodiment are used.

On the other hand, when the water-washing regenerative deodorizing filters of Comparative Examples 4 and 5 are used, it is understood that the deodorization performance is regenerated to only about half extent and thus the regeneration rate is low.

The reasons therefor include the following: a sufficient regeneration cannot be achieved when a low-temperature water like tap water is used, it is difficult to remove water thoroughly since an inclusion type deodorizing filter is poor in air permeability and thus is difficult to dry, and the like.

Moreover, from the results of the shape test, it is revealed that the water-washing regenerative filters of Comparative Examples 4 and 5 are difficult to maintain the shape thereof.

This is because water at water-washing is a large burden to the support and the shape distortion and the like are induced.

Thus, the water-washing type deodorizing filter requires a time-consuming washing operation but the regeneration efficiency is low. However, both of the test filter or the like operation, and it is possible to regenerate the deodorization performance only by applying a voltage.

According to the at least one embodiment of the invention, there is obtained a thermally regenerative deodorizing filter having a large deodorization capacity and capable of regeneration of the deodorization performance of the sealed deodorant and efficient repeated deodorization any number of times by heating the PTC heater placed at the inner core or liner part after use.

The following will show evaluation methods and evaluation results illustrating superiority of the fourth embodiment of the invention and will describe specific advantages of the fourth embodiment of the invention.

Ammonia Deodorization Performance Test

Each of the thermally regenerative deodorizing filter of Examples 8 and 9 and Comparative Examples 6 to 8 was mounted on an air cleaner for test. While the cleaner was operated in a closed vessel of 1 $m^3$, ammonia standard gas was gradually injected thereinto and the volume W (ml) of ammonia injected was determined until the ammonia concentration in the closed vessel detected using an ammonia gas sensor reached 20 ppm.

Then, each of the deodorizing filter of Examples and Comparative Examples was subjected to regeneration treatment by the method to be mentioned below. Thereafter, the deodorization test was again carried out in the same manner as above to determine the volume X (ml) of ammonia injected.

A value (X/W) obtained by dividing the volume of ammonia gas injected after regeneration by the initial volume of ammonia gas injected was determined and was defined as an ammonia-deodorizing regeneration rate (s).

Acetaldehyde Deodorization Performance Test

Each of the thermally regenerative deodorizing filter of Examples 8 and 9 and Comparative Examples 6 to 8 was mounted on an air cleaner for test. While the cleaner was operated in a closed vessel of 1 $m^3$, acetaldehyde standard gas was gradually injected thereinto and the volume Y (ml) of acetaldehyde injected was determined until the acetaldehyde concentration in the closed vessel detected using a VOC sensor reached 5 ppm.

Then, each of the deodorizing filters of Examples 8 and 9 and Comparative Examples 6 to 8 was subjected to regeneration treatment by the method to be mentioned below. Thereafter, the deodorizing test was again carried out in the same manner as above to determine the volume Z (ml) of acetaldehyde injected.

A value (Z/Y) obtained by dividing the volume of acetaldehyde gas injected after regeneration by the initial volume of acetaldehyde gas injected was determined and was defined as an aldehyde-deodorizing regeneration rate (%).

Regeneration Treatment (Thermal Regeneration by Electrification)

On the test bodies of Examples 8 and 9 and Comparative Example 8, after the test was finished in the ammonia deodorization performance test and in the aldehyde deodorization performance test, a voltage was applied to the terminals attached to the end of each honeycomb to electrify the PTC sheet or the adsorbent, whereby regeneration treatment was carried out for 180 minutes.

After the thermal regeneration, the test bodies were allowed to stand until the temperature thereof became to a room temperature.

Regeneration Treatment (Water-Washing Regeneration)

On the test bodies of Comparative Examples 6 and 7, in the ammonia deodorization performance test or in the aldehyde deodorization performance test, the deodorizing filters of examples and Comparative Examples used for the first measurement were individually immersed for 1 hour in an aqueous solution in which a standard amount of a commercially available household neutral detergent (trade name "Mamalemon", manufactured by Lion Corporation.) was 10 further diluted 10 times, then thoroughly rinsed by immersion for 1 hour while introducing tap water, and dried in the sun for 8 hours after draining off the water, whereby treatment for regenerating the deodorizing ability was carried out.

Shape Test

On each test body subjected to thermal regeneration treatment repeated 10 times, shape distortion was evaluated visually according to the following standard.

Evaluation Level

◉: No change is observed before test.

○: Slight distortion is observed.

Δ: Shape distortion and exfoliation at adhered part are observed.

X: Structure cannot be maintained.

A test was conducted by the above method. The results of evaluating the performance are shown in Table 4.

TABLE 4

| Example or Comparative Example | Aldehyde deodorization test (%) | Ammonia deodorization test (%) | Shape test |
|---|---|---|---|
| Example 8 | 100 | 98 | ◉ |
| Example 9 | 98 | 97 | ◉ |
| Comparative Example 6 | 67 | 62 | Δ |
| Comparative Example 7 | 58 | 65 | ○ |
| Comparative Example 8 | 47 | 31 | ◉ |

From the results of Table 4, it is understood that a regeneration efficiency of nearly 100% is obtained for both of aldehyde and ammonia when the thermally regenerative deodorizing filters of Examples 8 and 9 of the 10 fourth embodiment are used.

On the other hand, when the water-washing regenerative deodorizing filters of Comparative Examples 6, 7 and 8 are used, it is understood that the deodorization performance is regenerated to only about half extent and thus the regeneration rate is low.

The reasons therefor include the following: a sufficient regeneration cannot be achieved when a low-temperature water like tap water is used, it is difficult to remove water thoroughly since an inclusion type deodorizing filter is poor in air permeability and thus is difficult to dry, and the like.

Moreover, from the results of the shape test, it is revealed that the water-washing regenerative filters of Comparative Examples are difficult to maintain the shape thereof.

This is because water at water-washing is a large burden to the support and the shape distortion and the like are induced.

Thus, the water-washing type deodorizing filter requires a time-consuming washing operation but the regeneration efficiency is low. However, each of the test bodies of Examples does not require removal of the filter or the like operation, and it is possible to regenerate the deodorization performance only by applying a voltage.

Moreover, in the deodorizing filter of Comparative Example 8, the honeycomb base material itself has no electroconductivity and the deodorant is electrified. However, in the case that the deodorant is electrified, it is difficult to electrify the whole filter evenly since the electric current flows through only low resistant paths among paths short-circuited with the electroconductive nets at both ends and, in addition, it is impossible to apply heat necessary for regeneration of the deodorization performance, to the filter.

According to the at least one embodiment of the invention, there is obtained a thermally regenerative deodorizing filter having a large deodorization capacity and capable of regeneration of the deodorization performance of the sealed deodorant and efficient repeated deodorization any number of times by electrifying the PTC heater used as a honeycomb base material after use.

INDUSTRIAL APPLICABILITY

The thermally regenerative deodorizing filter of at least one embodiment of the invention can efficiently regenerate the deodorization performance by integrally comprising a deodorizing filter and a heating element. In particular, the use of a PTC heater as a heating heater part can realize a deodorizing filter having high safety and energy efficiency. Thus, the deodorizing filter has an extremely large industrial applicability.

The invention claimed is:

1. A thermally regenerative deodorizing filter comprising:
    a honeycomb base material of a deodorizing filter, which comprises at least a first kind of electroconductive sheet and a second kind of electroconductive sheet,
    a deodorant packed in a cell of the honeycomb base material, and
    a gas-permeable base material sealing openings at the both sides of the honeycomb base material,
    wherein at least one of said kinds of said electroconductive sheets comprises a PTC heater and at least one of said kinds of electroconductive sheets does not comprise a PTC heater.

2. The thermally regenerative deodorizing filter according to claim 1, wherein the PTC heater is a ceramic PTC heater.

3. The thermally regenerative deodorizing filter according to claim 1, wherein the PTC heater is an organic PTC heater.

4. A thermally regenerative deodorizing filter, which comprises a honeycomb base material, a deodorant packed in a cell of the honeycomb base material, and a gas-permeable base material which seals openings at the both sides of the honeycomb base material,
    wherein the honeycomb base material comprises a PTC heater, the gas-permeable base material comprises an electroconductive material, and the PTC heater is heated by applying a voltage between the gas-permeable base material.

5. The thermally regenerative deodorizing filter according to claim 4, wherein the PTC heater is a ceramic PTC heater.

6. The thermally regenerative deodorizing filter according to claim 4, wherein the PTC heater is an organic PTC heater.

7. The thermally regenerative deodorizing filter according to claim 1 wherein:
    at least one of the electroconductive sheets is a corrugated inner core part, and at least one of the electroconductive sheets is a liner part coupled to the at least one corrugated inner core part.

8. The thermally regenerative deodorizing filter according to claim 1 wherein the PTC heater is a self-temperature controlling type at an electrification.

9. The thermally regenerative deodorizing filter according to claim 4 wherein the PTC heater is a self-temperature controlling type at an electrification.

* * * * *